(12) United States Patent
Ku et al.

(10) Patent No.: US 9,008,340 B2
(45) Date of Patent: Apr. 14, 2015

(54) METHOD AND APPARATUS TO TEST HEARING ABILITY AND HEARING AID APPARATUS USING THE SAME

(75) Inventors: Yun-seo Ku, Seoul (KR); Jong-keun Song, Yongin-si (KR); Dong-wook Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 359 days.

(21) Appl. No.: 13/482,174

(22) Filed: May 29, 2012

(65) Prior Publication Data
US 2012/0300964 A1 Nov. 29, 2012

(30) Foreign Application Priority Data
May 26, 2011 (KR) .......................... 10-2011-0050189

(51) Int. Cl.
*H04R 25/00* (2006.01)
*A61B 5/12* (2006.01)
*A61B 5/0484* (2006.01)
*A61B 5/00* (2006.01)

(52) U.S. Cl.
CPC ............. *A61B 5/125* (2013.01); *A61B 5/04845* (2013.01); *A61B 5/6817* (2013.01); *H04R 25/305* (2013.01); *H04R 25/70* (2013.01); *H04R 2225/39* (2013.01); *H04R 2225/41* (2013.01)

(58) Field of Classification Search
USPC ...................... 381/317; 600/25, 544, 558, 559
See application file for complete search history.

(56) References Cited

U.S. PATENT DOCUMENTS

| | | | |
|---|---|---|---|
| 6,167,138 A | 12/2000 | Shennib | |
| 6,674,862 B1 | 1/2004 | Magilen | |
| 8,126,176 B2 * | 2/2012 | Iwano et al. | ................. 381/317 |
| 2008/0021517 A1 | 1/2008 | Dietrich | |
| 2008/0285780 A1 | 11/2008 | Aarts | |
| 2010/0160714 A1 * | 6/2010 | Chua et al. | ...................... 600/25 |
| 2010/0249635 A1 | 9/2010 | Van Der Reijden | |

FOREIGN PATENT DOCUMENTS

| | | |
|---|---|---|
| KR | 10-2008-0093611 A | 10/2008 |
| KR | 10-2009-0108373 A | 10/2009 |
| KR | 10-2010-0042370 A | 4/2010 |
| WO | WO 2011/006681 * 1/2011 | ............ H04R 25/00 |

* cited by examiner

*Primary Examiner* — Brian Ensey
(74) *Attorney, Agent, or Firm* — NSIP Law

(57) ABSTRACT

A method and apparatus to a hearing ability and a hearing aid using the same are described. The hearing aid outputs a sound to test a hearing ability of a user, to detect an electrical signal generated in a body of the user as a result of the output sound, amplifies the electrical signal detected by an electrode unit, and to determine an amplification ratio of a surrounding sound detected by the hearing aid based on characteristics of peaks of waveforms of the amplified signal.

17 Claims, 7 Drawing Sheets

METHOD AND APPARATUS TO TEST HEARING ABILITY AND HEARING AID APPARATUS USING THE SAME

CROSS-REFERENCE TO RELATED APPLICATIONS

This application claims the benefit of Korean Patent Application No. 10-2011-0050189, filed on May 26, 2011, in the Korean Intellectual Property Office, the disclosure of which is incorporated herein in its entirety by reference.

BACKGROUND

1. Field

The following description relates to a method and apparatus to test hearing ability and a hearing aid apparatus using the same.

2. Description of the Related Art

Hearing tests are classified into a subjective hearing test and an objective hearing test. According to the subjective test, an examinee's voluntary response to auditory stimulus is checked, and hearing ability of the examinee is determined based on the response. Therefore, in the case of the subjective hearing test, a subjective of the examinee may intervene in the response to an auditory stimulus, and the test result would be completely dependent on the subjective response of the examinee. On the contrary, in the case of the objective test, an electrical response of the examinee's body to an auditory stimulus is detected by an instrument to determine hearing ability of the examinee. Therefore, an emotion of an examinee does not intervene in the objective hearing test. Thus, in comparison with the subjective hearing test, the reliability of the objective hearing test is higher, and a test result may be quantitatively obtained. Examples of the subjective hearing test include pure-tone audiometry, speech reception threshold (SRT), and word recognition score (WRT). Examples of the objective hearing test include otoacoustic emission (OAE), electrocochleography (ECoG), and auditory brainstem response (ABR).

SUMMARY

In one general aspect, hearing test methods and apparatuses are provided to easily and rapidly conduct an objective hearing test.

In another general aspect, hearing aid apparatuses are provided to be configured to compensate for hearing loss of a user using the objective hearing test.

In one aspect, a computer program embodied on a non-transitory computer readable medium is provided, where the computer program is configured to control a processor to execute hearing test methods to easily and rapidly conduct an objective hearing test.

Additional aspects will be set forth in part in the description which follows and, in part, will be apparent from the description, or may be learned by practice of the presented embodiments.

According to an illustrative aspect, a hearing aid apparatus includes a sound output unit configured to output a sound for testing hearing ability of a user. The apparatus includes an electrode unit configured to detect an electrical signal generated in a body of the user as a result of the output sound. The apparatus also includes an amplification unit configured to amplify the electrical signal detected by the electrode unit. A processor in the apparatus is configured to determine an amplification ratio of a surrounding sound detected by the hearing aid apparatus based on characteristics of peaks of waveforms of the amplified signal.

According to another illustrative aspect, a method to test hearing ability includes receiving an electrical signal generated in a body of a user as a result of a sound to test the hearing ability of the user. The method also includes calculating a value of a parameter representing characteristics of peaks of waveforms of the electrical signal. The method also includes comparing the value of the parameter with a target value. The method includes determining whether the hearing ability is normal based on a comparison result.

According to another aspect, a non-transitory computer readable medium having stored therein a computer program is provided, where the computer program is configured to control a processor to execute a method to test hearing ability.

In one illustrative aspect, a method to compensate for hearing loss of a user using a hearing aid apparatus includes outputting a signal of an auditory stimulation sound to test a hearing ability of the user, and detecting an electrical signal as a result of the auditory stimulation sound. The method also includes amplifying the electrical signal detected, calculating a parameter value representing characteristics of peaks of waveforms of the electrical signal amplified, and comparing a difference between the parameter value and a target value with a predetermined range. When the difference is greater than the predetermined range, the method includes determining an amplification ratio for the auditory stimulation sound based on the difference between the parameter value and the target value and amplifying an auditory stimulation sound output for testing the hearing ability of the user based on the amplification ratio determined.

Other features and aspects may be apparent from the following detailed description, the drawings, and the claims.

BRIEF DESCRIPTION OF THE DRAWINGS

The above and other features and advantages of the present invention will become more apparent by describing in detail configurations thereof with reference to the attached drawings in which.

Figure 1:
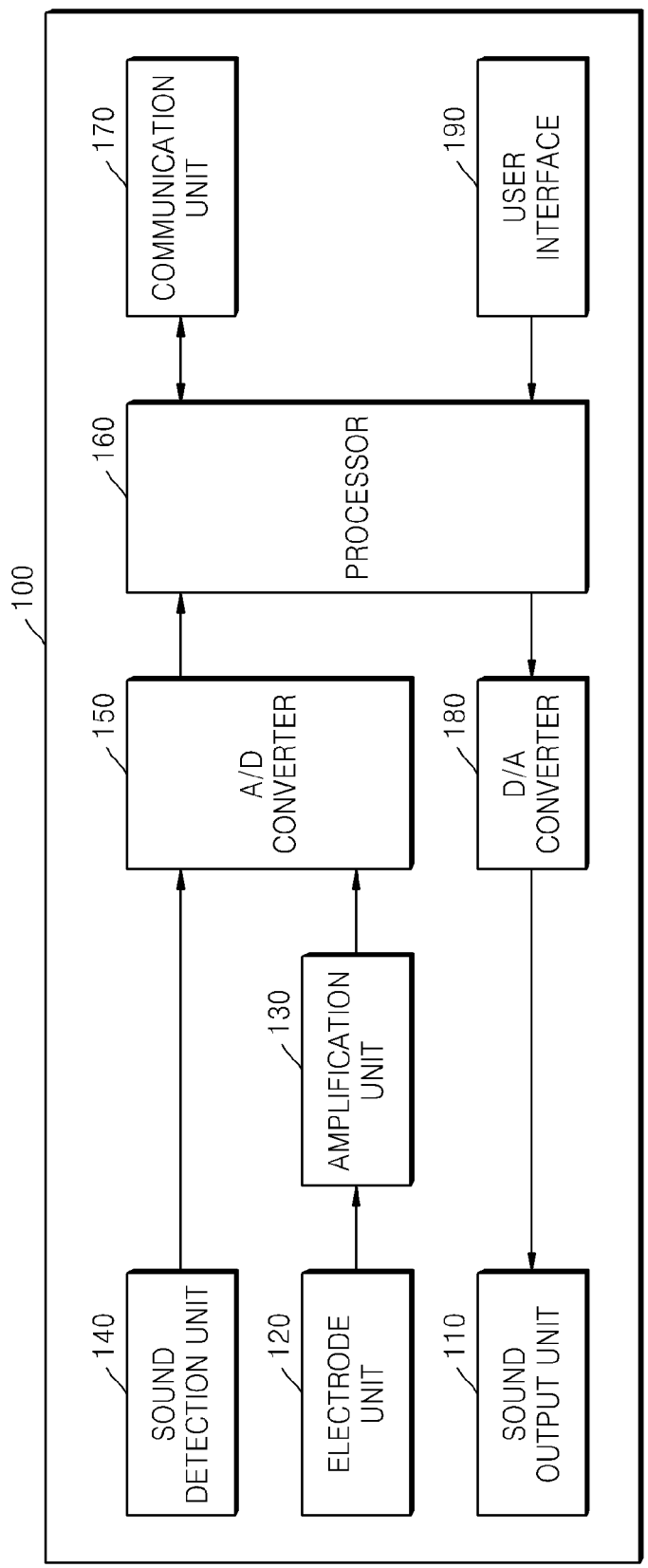
FIG. 1 is a block diagram illustrating an illustrative configuration of a hearing aid apparatus.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

Hereinafter, a hearing aid apparatus 100 will be described in detail with reference to the accompanying drawings.

FIG. 1 is a block diagram illustrating an illustrative configuration of the hearing aid apparatus 100. Referring to FIG. 1, the hearing aid apparatus 100 may include a sound output unit 110, an electrode unit 120, an amplification unit 130, a sound detection unit 140, an analog-to-digital (A/D) converter 150, a processor 160, a communication unit 170, a digital-to-analog (D/A) converter 180, and a user interface 190. The hearing aid apparatus 100 of FIG. 1 is a device which helps a user to improve a user's hearing ability. The hearing ability is an ability to hear through the ear. To aid hearing ability is to help the user better hear a sound in circumstances when the user's hearing ability is degraded or almost lost (hereinafter, referred to as loss of hearing). Compensating for hearing loss may be referred to as a process of detecting, amplifying, and modulating sound using a hearing aid apparatus to help a user compensate for the hearing loss and improve sound for the user to hear.

The hearing aid apparatus 100 may include a device for helping a user overcome hearing loss and improve hearing of a sound by compensating for the hearing loss. The hearing aid apparatus 100 may include a hearing aid that helps a user overcome hearing loss and improve hearing of a sound by compensating for the hearing loss. Hereinafter, for convenience of description, in the present embodiment, the hearing aid apparatus 100 indicates a hearing aid. However, it is obvious to one of ordinary skill in the art that the hearing aid apparatus 100 is not limited thereto.

In detail, the hearing aid apparatus 100 compensates for the user's hearing loss by detecting sounds around the user and by amplifying the detected sound. Generally, a sound amplification ratio of a hearing aid would be determined by an expert on hearing aids based on a result of a hearing test conducted at a hospital. Sound amplification ratio, in one example, may be a gain to amplify the input sound signal to provide the hearing impaired with louder output sound based on their hearing ability. In the configuration of the hearing aid apparatus 100, a hearing test is conducted using the hearing aid apparatus 100, and the hearing aid apparatus 100 instantly determines a sound amplification ratio, and outputs sounds amplified according to a sound amplification ratio to compensate for the user's hearing loss. That is, the hearing aid apparatus 100 conducts the hearing test automatically, without user intervention, and directly compensates for the hearing loss of the user using a result of the hearing test. Herein, the hearing aid apparatus 100 may conduct the hearing test to test a user's ability to hear sounds by measuring hearing characteristics of the user. The hearing characteristics of the user are data that represent information related to the user's hearing ability. On the basis of the information, the hearing aid apparatus 100 may determine a frequency band of sounds and a degree of sound loudness the user hears, a particular part of the auditory organ that may be abnormal, and whether a disease related to hearing ability may exist.

For example, the hearing aid apparatus 100 may acquire waveforms of electrical signals induced in the body of the user and transmitted through electrodes to conduct an objective hearing test and measure hearing characteristics of the user. Detailed descriptions of the objective hearing test will be given with reference to the processor 160. Also, after the hearing aid apparatus 100 may compensate for the hearing loss of the user according to a result of the hearing test, and may perform a checking process to check whether the sound amplification ratio determined by the processor 160 included in the hearing aid apparatus 100 is appropriate to compensate for the user's hearing loss. In addition, the hearing aid apparatus 100 may determine the sound amplification ratio, with which the hearing loss of a user is optimally compensated for, by repeating the checking process a predetermined number of times. Detailed descriptions of this operation will be given with reference to the processor 160.

Referring to FIG. 1, the sound output unit 110 outputs sounds to be heard by the user. The sound output unit 110 may be a speaker, a receiver of a hear aid, or the like. The sound output unit 110 outputs sounds that may be used to test the hearing ability of the user, and sounds that may be used to check whether a sound amplification ratio determined by the processor 160 is appropriate to compensate for the user's hearing loss. The sound detection unit 140 may detect the sounds, which may then be amplified according to the sound amplification ratio determined by the processor 160 to output hearing-loss-compensated sounds.

Once the sound output unit 110 outputs the sounds to test the user's hearing ability, the user's auditory organ transfers the sounds to the brain. The outputting of the sounds for the auditory organ to respond to sounds is referred to as applying an auditory stimulus in a hearing test. During the hearing test, the sound output unit 110 transmits the auditory stimulus to trigger nerve cells, which are related to the user's hearing ability (hereinafter, referred to as auditory nerve cells), to generate electrical signals. Detailed descriptions of this operation will be given with reference to the electrode unit 120.

Sounds for the auditory stimulus may include a click, a tone pip, and a tone burst, but are not limited thereto. For acquiring stable waveforms, or according to a type of hearing test, the hearing aid apparatus 100 needs to adjust the type, strength (dB), output interval (times/sec), retention time (μsec), and frequency (Hz) of the sound for the auditory stimulus. Therefore, the user interface 190, such as a switch or a wireless interface operatively connected to the hearing aid apparatus 100, may enable the user to select a type, strength, output interval, retention time, and frequency of the sound for the auditory stimulus to be output from the sound output unit 110. Accordingly, the sound output unit 110 may output a sound corresponding to the information input through the user interface 190. For example, the information input through the user interface 190 is transferred to the processor 160. Based on selected type of sound for the auditory stimulus, the processor 160 performs a signal processing operation on the selected sound to change a strength, output interval, retention time, and frequency thereof. Then, a signal of the processed sound is transferred to the sound output unit 110. The sound output unit 110 receives the signal to output the sound for the auditory stimulus.

In response, the sound output unit 110 outputs sounds to check whether a sound amplification ratio determined by the processor 160 is appropriate to compensate for the user's hearing loss. For instance, the sound output unit 110 is configured to output the sounds by applying the sound amplification ratio determined by the processor 160 to an auditory stimulation sound to test the user's hearing ability. That is, the processor 160 determines the sound amplification ratio based on a result of the hearing test, applies the determined sound amplification ratio to the auditory stimulation sound to test the user's hearing ability, and transfers the signal of auditory stimulation sound to which the sound amplification ratio is applied to the sound output unit 110. The sound output unit 110 outputs the auditory stimulation sound, to which the sound amplification ratio is applied, to conduct a test to check whether the sound amplification ratio determined by the processor 160 is appropriate to compensate for the user's hearing loss. Detailed descriptions of this operation will be given with reference to the processor 160.

Also, the sound output unit 110 amplifies sounds around the user, which are detected by the hearing aid apparatus 100, according to the sound amplification ratio determined by the processor 160 to output hearing-loss-compensated sounds. The hearing aid apparatus 100 receives a sound signal through the sound detection unit 140, and the received sound signal is transferred to the processor 160 to be amplified according to the sound amplification ratio. Then, the amplified sound signal is output through the sound output unit 110. Herein, the sound signal is an electrical signal to which a sound is converted, or an electrical signal which is converted to a sound. The user hears the hearing-loss-compensated sounds according to a result of the hearing test from the sound output unit 110.

The electrode unit 120 may be disposed on a body of the user to detect electrical changes of one or more nerve cells and muscle cells. The electrical changes of the nerve cells or muscle cells are induced by stimulus to the nerve cells or muscle cells. That is, if the nerve cells or muscle cells of the body are stimulated, electrical changes occur in the stimulated cells, and the electrical changes are transferred along neighboring nerve cells. The electrical change induced by stimulation is referred to as a generated potential. Hereinafter, an electrical signal, which represents the electrical change induced in a body of the user, is referred to as a potential.

In the case of auditory nerves, if an auditory stimulus is applied to the ear of the user, the auditory stimulus is transferred through vibration of air, and the vibration of air as a result of the sound stimulus is transferred to the tympanum to vibrate the tympanum. If the vibration of the tympanum is transferred to sensory reception cells of the cochlea, a potential is generated in the sensory reception cells. Herein, a generated potential change is transferred along the nerve cells to the central nervous system of the brain so that the brain recognizes a sound. That is, the potential change that occurs as a result of the auditory stimulus is transferred along auditory nerves, which are related to auditory sense, to the brain, and; thus, the brain recognizes a sound.

The potential generated in the user's body as a result of the auditory stimulus and detected by the electrode unit 120 is input to the amplification unit 130. The amplification unit 130 amplifies the potential detected by the electrode unit 120, and the processor 160 determines whether the user's hearing ability of the user is normal based on waveforms of the amplified potential. The amplification unit 130 acquires a signal required to measure hearing characteristics of the user using two or more potentials, for example, a potential of the nerve cells and a reference potential thereof. The two or more potentials are detected using two or more electrodes of the electrode unit 120. The electrode unit 120 includes a measuring electrode 211 for detecting a potential of the nerve cells, and a reference electrode 214 to detect a potential that is a reference for the potential of the nerve cells. The measuring electrode 211 and the reference electrode 214 are described with reference to FIG. 2.

Figure 2:
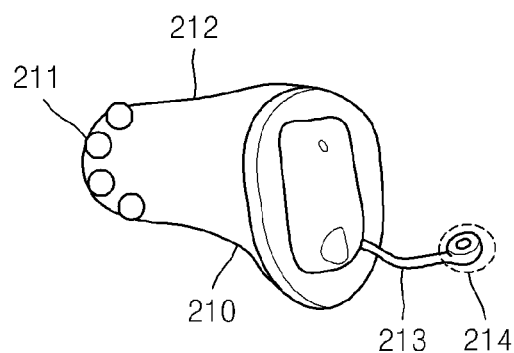
FIG. 2 illustrates an illustrative configuration of an electrode unit disposed on a hearing aid apparatus.

FIG. 2 illustrates an illustrative configuration of the hearing aid apparatus 100 of FIG. 1, including the electrode unit 120 to detect potentials. As illustrated in FIG. 2, the measuring electrode 211 detects one or more potentials of the nerve cells and the muscle cells. The measuring electrode 211 is disposed on a surface of the body of the user to detect the potential. For instance, according to an auditory brainstem response (ABR) test, which is an objective hearing test conducted using the hearing aid apparatus 100, a potential generated, while an auditory stimulus is transferred to the brainstem is measured. Therefore, the measuring electrode may be disposed on a scalp. As another example, according to electrocochleography (ECoG), which is another objective hearing test conducted using the hearing aid apparatus 100, a potential of cochlear nerves is measured. Therefore, the measuring electrode may be disposed on an external auditory meatus or tympanum adjacent to the cochlea.

The measuring electrode 211 may include one or more electrodes, and the number of channels increases according to the number of the electrodes. When an objective hearing test is conducted, all potentials of a plurality of the channels may be used, or only the largest potential from among the potentials may be selected to be used. Detailed descriptions of the channels will be given with reference to the processor 160. The reference electrode 214 detects a potential that is a reference for a potential detected by the measuring electrode 211. The reference electrode 214 may be used for multiple measuring electrodes 211, and a ground electrode (not shown) may be used as the reference electrode 214. The reference electrode 214 is positioned at a location to be least affected by the potential detected by the measuring electrode 211. The reference electrode 214 is also disposed on the surface of the body of the user to detect the potential of the body. For instance, when the ABR test is conducted, the reference electrode 214 may be disposed on the back of both ears. As another example, when the ECoG is conducted, the reference electrode 214 may be disposed on a forehead, or the back of the ear or neck so as to be far from the measuring electrode 211 as possible, which is adjacent to the cochlea. In an example, to position the reference electrode 214 at a location that is least affected by the potential of the measuring electrode 211, the reference electrode 214 may be connected to a connector 213, except for the electrodes of the electrode unit 120. Detailed descriptions of the connector 213 will be given below.

Except for the electrodes of the electrode unit 120, electrodes to detect a potential generated in the body of the user may be connected to the connector 213 to be disposed on the surface of the body to easily conduct a hearing test or acquire stable waveforms. In one example, the connector 213 may be an electric terminal that electrically connects a power source and a device, a device and another device, or a unit and another unit in a device. As illustrated in FIG. 2, the connector 213 may have a form of a wire that electrically connects the hearing aid apparatus 100 and an electrode, but is not limited thereto.

As illustrated in FIG. 1, the amplification unit 130 amplifies potential signals detected by the electrode unit 120. Because the potential signals detected by the electrode unit 120 are very small signals in units of μV, the hearing aid apparatus 100 amplifies the detected signals to measure hearing characteristics of the user using the potential signals. The amplification unit 130 receives the reference potential detected by the reference electrode 214 of FIG. 2 and the potential detected by the measuring electrode 211 of FIG. 2 to amplify a difference therebetween. For instance, the detected potential signals and the potential difference acquired from the detected potential signals may be analog signals having waveforms. The amplification unit 130 may amplify the analog signals using an analog amplifier. The amplification unit 130 may further include filters to acquire an amplified signal of a desired frequency band by filtering out undesired frequencies. Signals of a plurality of channels may be obtained from a plurality of measuring electrodes 211, each electrode would be configured as the electrode unit 120 as previously described. When the signals of a plurality of channels are used at the same time, the amplification unit 130 may obtain potential differences from the potential signals detected by the measuring electrodes 211, and may amplify and filter the potential differences. Therefore, when signals of a plurality of channels are simultaneously used, the amplification unit 130 may need amplifiers and filters as many as the number of the measuring electrodes 211.

Figure 3:
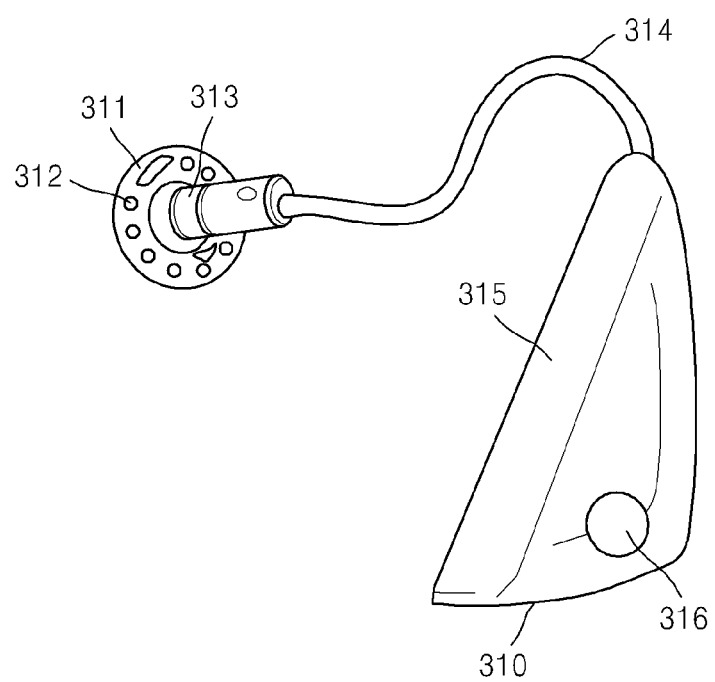
FIG. 3 illustrates another illustrative configuration of an electrode unit disposed on a hearing aid apparatus.

Also, the amplification unit 130 may be disposed as close as possible to the measuring electrode 211. The potential signals detected by the measuring electrode 211 are very small signals in units of μV, and, thus, are greatly influenced by noise. For the potential signals detected by the measuring electrode 211 to be only slightly influenced by noise, the amplification unit 130 may be disposed near the measuring electrode 211. Referring to FIG. 3 which illustrates an embodiment of the inventive concept, in the hearing aid apparatus 100 of FIG. 3, a housing 315, which includes a processor that compensates for hearing loss, and a receiver 313, which outputs a sound, are separated from each other and are connected to each other through a wire 314. In this example, only the receiver 313 separated from the housing 315 is inserted in an external auditory meatus. In one instance, when measuring electrodes 312 are disposed on the receiver 313, the amplification unit 130, which amplifies a difference between potential signals detected by the measuring electrodes 312, may be disposed inside the receiver 313 adjacent to the measuring electrodes 312 so as to be only slightly influenced by noise.

Resistances and capacitances of resistors and capacitors included in the amplifiers and filters of the amplification unit 130 may be changed. By changing the resistances and capacitances, an amplification gain and cut-off frequency of the hearing aid apparatus 100 may be adjusted. The amplification gain represents an amplification degree of a potential signal detected by the electrode unit 120. The very small potential signals detected by the electrode unit 120 are amplified for hearing characteristics of the user to become measurable. A degree of the amplification is referred to as the amplification gain. The cut-off frequency determines a frequency region in which potential signals detected by the electrode unit 120 are cut off. It will be understood by those of ordinary skill in the art that values of the amplification gain and cut-off frequency may be changed by using hardware, or by using software loaded in the processor 160 after conversion to digital signals. Also, it will be understood by those of ordinary skill in the art that the amplifiers and filters may be integrated into one chip to miniaturize the hearing aid apparatus 100.

The sound detection unit 140 detects a surrounding sound, and converts the detected sound to an electrical signal. The sound detection unit 140 may be a microphone. The hearing aid apparatus 100 amplifies the sound detected by the sound detection unit 140 for the user to hear the amplified sound which compensates for the hearing loss of the user. Therefore, the sound detection unit 140 converts the detected sound to an electrical signal, and transfers the electrical signal to the processor 160 of the hearing aid apparatus 100. The electrical signal to which the sound is converted is referred to as a sound signal. The processor 160 performs a signal processing operation, such as an amplification operation on the received sound signal, to output a hearing-loss-compensated sound, for instance, a sound hearable by the user.

The A/D converter 150 converts an analog signal received from the amplification unit 130 to a digital signal, and outputs the converted digital signal. The A/D converter 150 outputs the converted digital signal to the processor 160 so that a digital signal processor (DSP) of the processor 160 may process the digital signal.

The processor 160 measures hearing characteristics of the user using the converted digital signal received from the A/D converter 150, determines whether the hearing ability of the user is normal on the basis of the measured hearing characteristics, and determines an amplification ratio of the sound detected by the sound detection unit 140. Also, a frequency, loudness level, and output interval of the sound to test hearing ability of the user are adjusted. The sound amplification ratio is applied to the sound to test the hearing ability of the user, and the sound amplified according to the amplification ratio is output to the sound output unit 110. The amplification ratio represents a sound amplification degree which determines to what level of loudness the sound detected by the sound detection unit 140 is amplified for the user to hear the sound well.

An amplification method of the hearing aid apparatus 100 is classified into an analog amplification method and a digital amplification method. According to the analog amplification method, an amplification ratio for an analog signal of a detected sound may be adjusted to compensate for the user's hearing loss. According to the digital amplification method, an analog signal of a detected sound may be converted to a digital signal, and an amplification ratio for the digital signal is adjusted to compensate for the hearing loss. More various and complex signals may be processed by using a digital signal in comparison with the use of the analog signal. For instance, in a digital filter, a digital signal may be divided into multiple channels of low and high frequency band so as to be individually amplified and controlled. Also, complex signal processing, such as noise elimination or sound reecho elimination is possible. According to the analog amplification method, an amplification ratio may be relatively precisely adjusted by adjusting the amplification ratio of an analog signal using a computer. However, there is a limitation in eliminating reecho or precisely compensating for serious hearing loss of a patient with sensorineural deafness. Therefore, the digital amplification method may be adopted for the hearing aid apparatus 100. However, it will be understood by those of ordinary skill in the art that the digital amplification method performed by the processor 160 may be substituted with the analog amplification method of the amplification unit 130.

The processor 160 of the hearing aid apparatus 100 includes a DSP to perform a digital signal processing operation. The DSP performs operations to adjust frequencies, magnitudes, and output intervals of signals and to compare values of signals at high speed. Therefore, the processor 160 performs digital signal processing operations such as amplifying and filtering a digital signal, eliminating noise of a signal, and a comparison operation. Also, the hearing aid apparatus 100 may divide a frequency band into several sections using the DSP to complexly and minutely adjust a sound. Each section is referred to as a channel. The hearing aid apparatus 100 adjusts a compression ratio, knee point, attack time, and release time for each channel to nonlinearly amplify a sound so that the user may comfortably hear a sound. For instance, through a channel, the hearing aid apparatus 100 may adjust surrounding sounds detected by the sound detection unit 110 so that low sounds may be heard quietly and high sounds may be heard loudly. Detailed descriptions of this operation will be understood by those of ordinary skill in the art.

The processor 160 measures the hearing characteristics of the user using signals amplified from potential signals detected by the electrode unit 120. The hearing characteristics of the user are data that represent information related to the hearing ability of the user. On the basis of the information, it may be determined what frequency band of sounds and to what degree of sound loudness the user may hear, what part of the auditory organ is abnormal, and whether a disease related to hearing ability exists. The hearing characteristics of the user may be measured using parameters that represent characteristics of peaks of the amplified signals. Herein, the characteristics of peaks may represent generation times of peaks of the amplified signals and signal magnitudes at the peaks. For example, to measure the hearing characteristics of the user, the processor 160 receives the amplified signals, and detects peaks of waveforms of the amplified signals. The detection of peaks may be performed by obtaining one arbitrary point (n) for a certain period of time and by comparing a magnitude of the arbitrary point (n) with that of another point (n-dt). This is a basic algorithm for detecting peaks, and it will be understood by those of ordinary skill in the art that various algorithms besides the above-described algorithm may be used.

Next, the processor 160 calculates values of the parameters that represent characteristics of the detected peaks. The calculated values may be hearing characteristics of the user. The parameters which represent the characteristics of peaks may be generation times of the peaks, signal magnitudes at the peaks, and ratio of peaks. The generation times of peaks represent the elapsed times from when an auditory stimulus is applied through the sound output unit 110, to when the peaks of waveforms are generated, and may be measured in milliseconds. The signal magnitudes at peaks represent amplitudes at peaks, and may be measured in microvolts. The ratio of peaks represents a ratio of amplitudes of peaks, and may be measured in microvolts. The hearing characteristics of a user may be values calculated for multiple parameters. Also, the hearing characteristics of the user may be values calculated for each of a plurality of frequencies. The hearing aid apparatus 100 outputs a sound to test the hearing ability of the user for each of a plurality of frequencies through the sound output unit 110, and the processor 160 detects peaks of signals amplified and input for each of a plurality of frequencies and calculates values of parameters that represent the peaks to obtain the values calculated for each of the plurality of frequencies. Hereinafter, for illustrative purposes, it may be assumed that the parameters which represent the characteristics of the peaks are signal magnitudes at the peaks.

The processor 160 determines whether the hearing ability of the user is normal using the measured hearing characteristics of the user. The processor 160 detects the peaks, and calculates values for the parameters that represent signal magnitudes at the peaks. Then, the processor 160 compares the values calculated for the signal magnitudes at the peaks with a target value to then determine whether the hearing ability of the user is normal. For example, the target value may be acquired by measuring hearing characteristics of people having normal hearing ability using the hearing aid apparatus 100. The hearing aid apparatus 100 calculates values of signal magnitudes at the peaks of waveforms of amplified signals by detecting potential signals generated in bodies of people having normal hearing ability. The calculated values represent hearing characteristics of people having normal hearing ability, and an average of the calculated values is the target value.

When a difference between the calculated value and the target value is within a predetermined permissible range, the processor 160 determines that the hearing ability of the user is normal. On the contrary, when the difference between the calculated value and the target value is out of the predetermined permissible range, the processor 160 determines that the hearing ability of the user is abnormal. Therefore, the hearing ability may be determined to be normal by comparing a difference between the calculated value and the target value with the predetermined permissible range. If hearing characteristics of the user are included in the permissible range, the hearing ability of the user is normal. If the hearing characteristics of the user are not included in the permissible range, the hearing ability of the user is abnormal. Thus, the predetermined permissible range is a reference for determining whether the hearing ability of the user is normal. That is, the predetermined permissible range is a normal range of hearing ability. The normal range of hearing ability may be determined by using various methods.

For instance, the normal range of hearing ability may be determined by calculating standard deviation or standard error of parameter values which represent hearing characteristics of people having normal hearing ability. The standard deviation is an average of deviations between measured values and an average value. That is, the standard deviation represents a standard distance from an average value. The standard error may be calculated by using the standard deviation and a sample size. In one example, the sample size represents the number of people having normal hearing ability, and the standard error represents a difference between an average of population and an average of sample group. That is, the standard error may indicate how well the average of sample group represents the average of population. Therefore, the normal range of hearing ability represents permissible deviation of a value of hearing characteristics from an average of hearing characteristics of people having normal hearing ability. A degree of the deviation from the average may be calculated using a standard deviation in a single sample, or using a standard error by selecting a plurality of samples. Calculations of the standard deviation and standard error will be understood by those of ordinary skill in the art, and, thus, detailed descriptions thereof are not provided. It will be understood by those of ordinary skill in the art that the normal range of hearing ability is not limited to the above described calculation method by using standard error, and that there are various other methods.

Also, it may be determined that the hearing ability of a user is not normal for each of a plurality of frequencies. The hearing aid apparatus 100 may output a sound to test the hearing ability of the user for each of a plurality of frequencies through the sound output unit 110. The processor 160 may detect peaks of signals amplified and input for each of a plurality of frequencies and calculates values of parameters which represent characteristics of the peaks to obtain values calculated for each of a plurality of frequencies. The processor 160 may compare the values calculated for each of a plurality of frequencies with a target value for each frequency to determine whether hearing ability of the user is normal for each frequency. In one example, abnormal hearing ability may be defined as loss in hearing ability of the user. Abnormality of hearing ability may represent that a particular auditory organ is abnormal or that there is a particular auditory disease according to specifically measured hearing characteristics of the user, for example, according to a kind of parameter which represents characteristics of peaks. This will be described in detail with reference to FIGS. 6 and 7.

The processor 160 may determine an amplification ratio for a sound detected by the sound detection unit 140 on the basis of the characteristics of peaks of waveforms input to the processor 160. That is, the processor 160 may calculate and determine the sound amplification ratio according to a difference between a parameter value for signal magnitudes at the peaks and a target value. The sound amplification ratio may be calculated using hearing characteristics of people having hearing loss. For instance, a formula for converting a difference between the calculated value and a target value to a sound amplification ratio may be obtained using the hearing aid apparatus 100 to calculate values that represent hearing characteristics of people having hearing loss, and by comparing the calculated values with a sound amplification ratio which is determined by using a typical test method. The processor 160 may determine a sound amplification ratio using this formula.

Also, the processor 160 may determine an amplification ratio for each of a plurality of frequencies by calculating the amplification ratio for each frequency on the basis of calculated values for signal magnitudes at peaks of waveforms of the signal. The hearing aid apparatus 100, which determines the amplification ratio for each of a plurality of frequencies, adjusts an amplification amount for a sound detected by the sound detection unit 140 to amplify the sound. This is similar to an equalizer function of an audio, which converts a sound for personal preference by adjusting a sound state of a particular frequency band after dividing a sound into several frequency bands.

Also, the hearing aid apparatus 100 tests whether the determined amplification ratio appropriately compensates for the user's hearing loss, and determines a new amplification ratio according to a result of the test. The hearing aid apparatus 100 repeats this operation a predetermined number of times to determine the amplification ratio that appropriately compensates for the hearing loss. An auditory stimulation sound is amplified according to the amplification ratio determined while the hearing aid apparatus 100 tests the hearing characteristics of the user, and a 3 is calculated again by using an electrical signal generated due to the amplified auditory stimulation sound. This operation is repeated until a difference between the calculated value and a target value is lower than a predetermined permissible range to determine the amplification ratio that appropriately compensates for the hearing loss of the user. That is, the hearing aid apparatus 100 amplifies an auditory stimulation sound to test the hearing ability based on the amplification ratio determined, using an electrical signal generated as a result of a sound testing the hearing ability of the user. The hearing aid apparatus 100 also determines a new amplification ratio by calculating the parameter value once again using an electrical signal generated based on the amplified auditory stimulation sound. The hearing aid apparatus 100 further amplifies the auditory stimulation sound to test the hearing ability of the user again according to the new amplification ratio. By repeating this operation of determining the new amplification ratio, the amplification ratio which appropriately compensates for the hearing loss of the user is determined when a difference between the calculated parameter value and a target value is lower than a predetermined permissible range.

Also, the processor 160 repeats the test, a predetermined number of times, to determine whether the determined amplification ratio appropriately compensates for the hearing loss of the user to produce an optimal amplification ratio. The optimal amplification ratio compensates for the user's hearing loss most effectively. An amplification ratio, which has a parameter value closest to a target value from among the amplification ratios determined during the repeated process, becomes an optimal amplification ratio. The processor 160 amplifies an auditory stimulation sound to test hearing ability from the sound output unit 110 according to the determined amplification ratio, and transfers the amplified sound signal to the sound output unit 110. The processor 160 repeats a process of calculating a parameter value using an electrical signal generated as a result of the amplified auditory stimulation sound, and determines the amplification ratio on the basis of a difference between the calculated parameter value and a target value. By repeating this process a predetermined number of times, the processor 160 determines an amplification ratio at which the calculated parameter value is closest to a target value. The hearing aid apparatus 100 applies such an optical amplification ratio to output a sound which is most effective for the hearing characteristics of the user.

The processor 160 stores the newly determined amplification ratio. The processor 160 compensates for the hearing loss by amplifying the sound detected by the sound detection unit 140 according to the sound amplification ratio stored in a memory included in the processor 160. Therefore, the processor 160 stores the newly determined amplification ratio from the processor 160 into the internal memory, and the hearing aid apparatus 100 compensates for hearing loss according to the newly determined amplification ratio. When the processor 160 stores the newly determined amplification ratio in the internal memory, data of a previous amplification ratio may be stored in additional memory regions for the user to see the data. Also, the user may manually adjust a sound amplification ratio through the user interface 190 of the hearing aid apparatus 100.

The processor 160 transmits a sound signal to the sound output unit 110. The sound signal is amplified from a sound detected by the sound amplification unit 140, according to the amplification ratio stored in an internal memory. The sound signal transmitted to the sound output unit 110 is converted into a sound by the sound output unit 110 to be output to the user's ear. For example, the hearing aid apparatus 100 amplifies the sound detected by the sound detection unit 140 according to the amplification ratio stored in the processor 160 and outputs a hearing-loss-compensated sound. Accordingly, the user hears a sound which compensates for the hearing loss according to the hearing characteristics of the user.

Also, the processor 160 performs a signal processing operation to adjust the type, strength, output interval, retention time, and frequency of an auditory stimulation sound for testing the hearing ability of the user. To obtain a hearing test result with stable waveforms, the adjustment of the type, strength, output interval, retention time, and frequency of an auditory stimulation sound is needed. Therefore, the processor 160 may receive the type, strength, output interval, retention time, and frequency of an auditory stimulation sound to be output from the sound output unit 110 using the user interface 190 such as a switch operatively connected to the hearing aid apparatus 100. Then, according to the received information, the processor 160 may perform a signal processing operation to select the type of auditory stimulation sound and change the strength, output interval, retention time, and frequency of the auditory stimulation sound.

The processor 160 determines whether the hearing ability is normal, and outputs a signal representing a result of the determination. The signal representing the result of determination may be transmitted to the sound output unit 110, or to the communication unit 170 of the hearing aid apparatus 100.

That is, the user may check the result of determining whether hearing ability is normal through the sound output unit 110 of the hearing aid apparatus 100, or through an external device which receives the result of determination from the communication unit 170. Also, the processor 160 may transmit not only the result of determination, but also calculated values of parameters to an external device through the communication unit 170 of the hearing aid apparatus 100. These parameters may represent characteristics of peaks of waveforms of the amplified signal and the waveforms of the amplified signal, for example, the hearing characteristics of the user.

The communication unit 170 transmits a result of the hearing test of the hearing aid apparatus 100 to an external device. The result of the hearing test may be a result of determining whether hearing ability is normal, as determined by the processor 160. In an alternative, the results of the hearing test may be values obtained for parameters that represent characteristics of peaks of waveforms of the amplified signal or the waveforms of the amplified signal, for example, the hearing characteristics of the user. It will be understood by those of ordinary skill in the art that the external device which receives the result of the hearing test may include a display device for displaying the result on a screen, and may include another device for displaying the result of the hearing test.

The D/A converter 180 converts a digital signal received from the processor 160 to an analog signal, and outputs the analog signal. The D/A converter 180 receives a digital signal on which a signal processing operation is performed, converts the digital signal to an analog signal, and transmits the analog signal to the sound output unit 110. The sound output unit 110 receives the converted analog signal from the D/A converter 180 to output an amplified sound.

In an illustration using the hearing aid apparatus 100 shown in FIG. 1, hearing characteristics of the user may be modeled. The hearing characteristics of the user are data that represents information related to the hearing ability of a user. On the basis of the information, it may be determined the frequency band of sounds and the degree of sound loudness the user hears, the part of the auditory organ that is abnormal, and whether a disease related to hearing ability exists. The hearing aid apparatus 100 illustrated in FIG. 1 performs an objective hearing test to measure the hearing characteristics of the user. The hearing test is conducted to test the ability of the user to hear sounds through the ear. Through the hearing test, a degree and type of hearing loss may be determined. To determine the degree of hearing loss, the extent to which hearing ability is degraded is checked in comparison with normal hearing ability, and sound of a frequency band between high frequency and low frequency that is not well heard is also checked. The type of hearing loss represents the part of a sound-progressing path that is not normal. That is, the type of hearing loss represents the part of the external ear, middle ear, internal ear, and auditory nerves that is not normal. When the external ear or middle is not normal, the type of hearing loss is conductive hearing loss. If the internal ear is not normal, the type of hearing loss is sensorineural hearing loss. Complex abnormality is mixed hearing loss. Therefore, on the basis of a result of hearing test conducted by using the hearing aid apparatus 100, the degree and type of hearing loss of the user may be obtained. Also, unlike a subjective hearing test in which an examinee recognizes a stimulation sound and responds for himself, a quantitative and objective test result may be obtained by conducting an objective hearing test. According to the subjective hearing test, a test result completely depends on a subjective response of an examinee. Thus, the subjective hearing test may be emotionally influenced by an examinee according to the health condition and awareness of an examinee, or a surrounding noise may influence the subject hearing test. Therefore, it is difficult to obtain a correct result. Moreover, the subjective hearing test is not suitable for a newborn baby, child, or mental patient who has difficulty in recognizing a sound and responding. However, by using an objective hearing test in which an electrical response of a body of an examinee to a stimulation sound is detected by an instrument, a correct and reliable test result may be obtained.

Furthermore, a hearing test for a non-communicative patient may be easily and rapidly conducted. Also, a result of a hearing test may be quantized so that hearing characteristics of a user may be modeled. By using a quantitative and objective result of a hearing test, results of periodic hearing tests of the user may be compared with each other. Thus, the hearing characteristics of the user may be periodically modeled. Particularly, in the case of patients with progressive hearing loss or patients with sudden hearing loss due to abrupt noise, a progress of hearing loss needs to be observed using results of regular hearing tests. Thus, the hearing aid apparatus 100 illustrated in FIG. 1 may be used to observe the progress of hearing loss by periodically modeling hearing characteristics. Also, in the case of patients under the age of 5 with hearing loss, hearing ability influences brain development. Thus, direction of language and pronunciation training needs to be set according to each stage of brain development. By using the hearing aid apparatus 100 illustrated in FIG. 1, periodically modeling of hearing characteristics may be used for setting direction of language and pronunciation training. Furthermore, the data obtained by periodically modeling of hearing characteristics of the user using the hearing aid apparatus 100 illustrated in FIG. 1 may also be used for determining a prognosis or observing progress after auditory surgery or treatment.

Hearing characteristics of the user may be modeled by calculating values for parameters which represent characteristics of peaks of signal waveform obtained by using the hearing aid apparatus 100, and by arranging the calculated values for each frequency. By using the modeled hearing characteristics, it may be determined whether the hearing ability of the user is impaired for each frequency, what type of hearing loss the user has, and whether there is an auditory disease. Also, by modeling and comparing the hearing characteristics of the user on a regular basis, it may be traced and understood whether there is sudden hearing loss and how serious hearing loss due to aging is. In the embodiment illustrated in FIG. 1, the processor 160 may compensate for the hearing loss of the user by adjusting a sound detected by the sound detection unit 140 based on the modeled hearing characteristics of the user.

Figure 5:
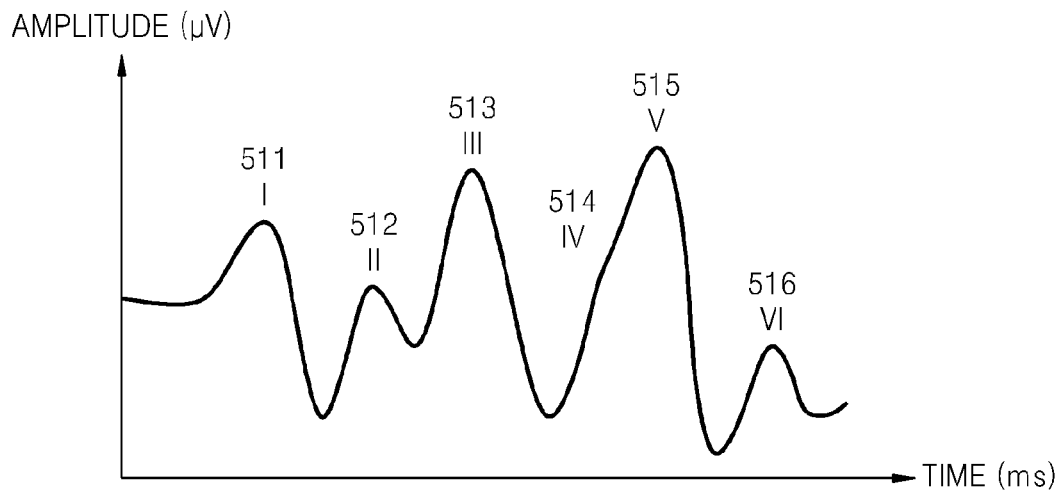
FIG. 5 illustrates a result of an auditory brainstem response (ABR) test conducted using the hearing aid apparatus illustrated in FIG. 1, and a graph of waveforms of signals detected by an electrode unit of FIG. 1.

In another embodiment using the hearing aid apparatus 100 illustrated in FIG. 1, an auditory brainstem response (ABR) test, which is an objective hearing test, may be conducted. According to the ABR test, a stimulation sound such as click sound is applied to the ear of an examinee, and an electrical change, i.e., a potential, generated in multiple parts of the nerve cells and brainstem of the examinee because of the stimulation sound is measured by using an electrode disposed on the scalp. In detail, for each frequency, the strength, stimulation interval, and frequency of the stimulation sound are adjusted to detect a potential generated as a result of the stimulation sound. Potentials are detected as a result of the ABR test, and a waveform generally includes 6 to 7 waves (ABR waves). Each wave represents a response in a transferring path of an auditory organ. Typical forms of the ABR waves are illustrated in FIG. 5. The ABR waves appear within about 10 msec after applying a stimulation sound. The ABR waves are recorded in the time domain, and have magnitudes smaller than about 1.0 µV. The most stable wave form is a wave V, which is used to measure hearing threshold. By using the waves I, III, and V, it may be determined whether there is a tumor in the auditory nerves, and retrocochlear lesions may be diagnosed. Also, a result of the ABR test is used to test functions of peripheral nerves and central nerves of patients in an intensive care unit and to monitor functions of cochlear and auditory nerves after surgery related to nerves.

In another embodiment using the hearing aid apparatus 100 illustrated in FIG. 1, electrocochleography (ECoG), which is an objective hearing test, may be conducted. According to the ECoG, a stimulation sound such as click sound is applied to the ear of an examinee, and a potential generated in the cochlea and cochlear nerves by the stimulation sound is measured using an electrode. The ECoG is classified into round window recording, transtympanic recording, tympanic recording, and extratympanic recording according to a position of an electrode. The round window recording and transtympanic recording are invasive methods for measuring a potential by inserting an electrode inside the tympanum. The tympanic recording and extratympanic recording are non-invasive methods for measuring a potential by disposing an electrode on the tympanum or external auditory meatus. According to the invasive method, a clear potential may be measured with little influence of noise. However, because the tympanum is penetrated to dispose an electrode, the examinee may be uncomfortable. However, with improvements in measuring techniques, a potential may be stably measured using a non-invasive method. Thus, a non-invasive method is widely used for the ECoG. For the ECoG using the hearing aid apparatus 100 illustrated in FIG. 1, a non-invasive method is used. Similarly to the ABR test, the strength, stimulation interval, and frequency of a stimulation sound are adjusted for each frequency to obtain a test result according to the ECoG. Potentials (endocochlear potentials) are detected by an electrode as a result of the ECoG have a waveform, and include cochlear microphonics (CM), a summating potential (SP), and a compound action potential (AP or CAP). Herein, the CM and SP are generated in outer hair cells of the cochlea, and the AP is generated in the auditory nerve cells. The CM, which is firstly generated among the three potentials, is an alternating potential which is instantly generated when a stimulation sound arrives at the cochlea. However, because a variation of the CM is large as a result of external noise and position of the electrode, the CM is not usually used. Therefore, for easily detecting the SP, the CM is suppressed using an alternating click phase. Typical waves of potentials within the cochlea include the AP and SP with suppression of the CM. Typical waves of potentials within the cochlea are described with reference to FIG. 6. The potentials within the cochlea are waves which appear within about 5 msec after applying a stimulation sound (magnitude in microvolts), and are recorded in the time domain. The SP is a direct current (DC) potential which appears in synchronization with a retention time of a stimulation sound, and has a negative value (−SP). The AP is an alternating current (AC) potential which represents overall reaction of cochlear nerve fibers. For example, in instances where the potential waves of the AP or SP within the cochlea are used, hearing thresholds of patients or infants, for whom the hearing test is difficult to conduct, may be measured. Also, hearing thresholds of patients with a central nervous system disease and patients with severe hearing loss, for whom correct hearing thresholds are not obtained by conducting a subjective hearing test and the ABR test, may be obtained. Also, a ratio of SP to AP (SP/AP ratio) may be calculated from the potential waves within the cochlea, and may be used for diagnosing and observing labyrinthine hydrops such as Meniere disease. The SP/AP ratio is also used for early diagnosing and prognosing sudden hearing loss as a result of noise.

In another embodiment using the hearing aid apparatus 100 illustrated in FIG. 1, a hearing threshold may be measured. The hearing threshold represents a minimum stimulation sound to which a body responds when a stimulation sound is applied, and is measured in decibel (dB). The hearing threshold may be measured by conducting a test for determining to what level of loudness a user hears for each frequency. By using the hearing threshold, hearing loss for each frequency may be obtained. When the hearing threshold measured for each frequency is included in a range of about 0 dB to about 20 dB (hereinafter, referred to as a normal range of hearing threshold), hearing ability of a corresponding frequency is normal. When the hearing threshold is out of this range, hearing ability is classified to mild hearing loss, moderate hearing loss, or severe hearing loss. The hearing threshold may be measured using the wave V of the ABR test, or a value of the SP or AP of the ECoG. The processor 160 of the hearing aid apparatus 100 gradually decreases intensity of a stimulation sound to test the hearing ability of the user, and outputs the decreased stimulation sound to the sound output unit 110. The processor 160 may compare generation times of peaks of waves of a signal generated and amplified as a result of a stimulation sound output from the sound output unit 110, and signal magnitudes at peaks at each intensity. In the alternative, the processor 160 may repeat a measurement to compare generation times of peaks of waves and signal magnitudes at peaks for each intensity so that the hearing threshold is obtained by recording the intensity of a stimulation sound that has a remarkably distorted value. The hearing aid apparatus 100 may repeat the same process for another frequency to measure a hearing threshold for each frequency. The hearing aid apparatus 100 may determine whether hearing ability is normal by comparing the measured hearing threshold with the normal range of the hearing threshold. When the measured hearing threshold is out of the normal range, it is determined that hearing loss for a corresponding frequency exists.

Referring to FIG. 2, the hearing aid apparatus 100 may be an in-the-ear (ITE) type hearing aid 210. The measuring electrode 211 and reference electrode 214 may be installed on the ITE type hearing aid 210. In FIG. 2, the measuring electrode 211 may be disposed on the receiver 212, which is closest to the tympanum when the ITE type hearing aid 210 is inserted in the ear. The ITE type hearing aid 210 may detect a correct potential signal which represents the user's hearing ability by disposing the measuring electrode 211 near the tympanum. Also, the reference electrode 214 may be disposed on the back of the ear or neck by being connected to the connector 213 so as to be only slightly influenced by a potential detected by the measuring electrode 211 as illustrated in FIG. 2. In the case of the hearing aid apparatus 100, all or part of which is inserted in the ear, an electrode may be disposed similarly to that of FIG. 2.

FIG. 3 illustrates another illustrative configuration of the hearing aid apparatus 100 of FIG. 1 in which an electrode to detect potentials is implemented. The hearing aid apparatus 100 illustrated in FIG. 3 is a receiver-in-the-canal (RIC) type hearing aid 310. The receiver 313 is separated to be inserted in the external auditory meatus. The measuring electrode 312 and reference electrode 316 are implemented in the RIC type hearing aid 310 disposed in the external auditory meatus. Because the measuring electrode 312 may detect a more accurate potential signal, which corresponds to the hearing ability of the user, when the measuring electrode 312 is closer to the tympanum, the measuring electrode 312 may be disposed on the receiver 313 or a rubbery ear dome 311 surrounding the receiver 313. The receiver 313 and the rubbery ear dome 311 are closest to the tympanum when the RIC type hearing aid 310 is worn. Also, the reference electrode 316 may be connected to the wire 314, and may be disposed on the housing 315, which includes an internal component disposed on the back of the ear to reduce the influence of the measuring electrode 312. Also, to prevent diminution of potential detected by the measuring electrode 312 and to reduce the influence of noise, the amplification unit 130 may be disposed in the receiver 312 which is close to the measuring electrode 312. In the case of the hearing aid apparatus 100 of which the receiver 313 is separated to be inserted in the external auditory meatus, an electrode and an amplification unit may be disposed similarly to those of FIG. 3.

Figure 4:
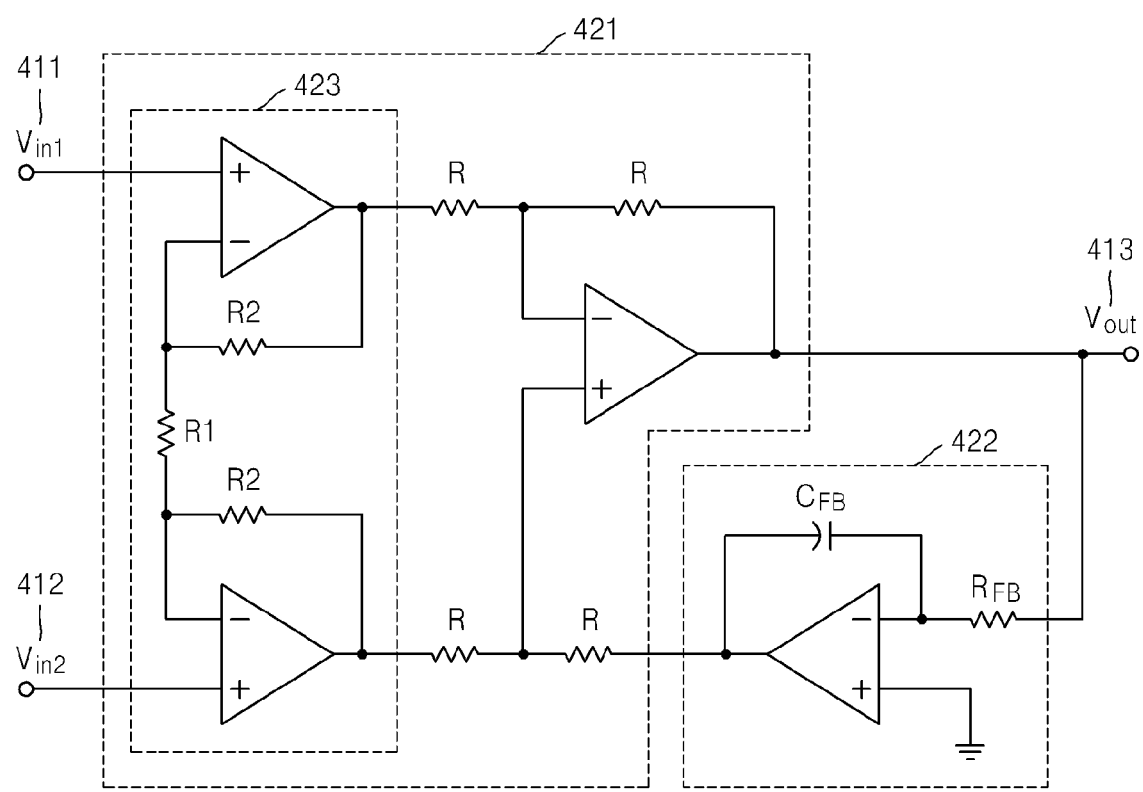
FIG. 4 is a circuit diagram illustrating an example of an amplification unit illustrated in FIG. 1.

FIG. 4 is a schematic circuit diagram illustrating an example of the amplification unit illustrated in FIG. 1. In the circuit, voltages Vin1 (411) and Vin2 (412) are input, and a voltage Vout (413) is output. The circuit of FIG. 4 includes a differential amplifier 421 and a low pass filter LPF 422 for feedback. A potential detected by the measuring electrode is input to one input terminal 411 of the differential amplifier 421, and a potential detected by the reference electrode is input to the other input terminal 412. A difference between a potential of the measuring electrode 211 and a potential of the reference electrode 214 is amplified and filtered to be output as an output Vout (413). By changing resistors and capacitors installed in the circuit, an amplification gain and cut-off frequency which determines a filtered-out frequency band may be adjusted. Resistances and capacitances for determining the cut-off frequency and amplification gain may be calculated by using the following equation.

$$Vout = \left(1 + \frac{2R_2}{R_1}\right)(V_{in1} - V_{in2})\frac{jwR_{FB}C_{FB}}{1 + jwR_{FB}C_{FB}}, f_L = \frac{1}{2\pi C_{FB}R_{FB}} \quad (1)$$

It will be understood by those of ordinary skill in the art that the above equation is typically used for calculating cut-off frequency and amplification gain in a differential amplifier and a filter connected for feedback. Thus, detailed descriptions are not provided. Values of the amplification gain and cut-off frequency may be changed using hardware, or using software loaded in the processor 160 after conversion to digital signals. Also, for miniaturizing the hearing aid apparatus 100, two operational amplifiers 423 on a front stage of the circuit may be eliminated. For microminiaturizing the hearing aid apparatus 100, an amplifier and a filter may be integrated into one chip. When potential signals are detected by one or more measuring electrode 211 at the same time, the amplification unit 130 needs the same number of differential amplifiers 421 and low pass filters 422 as that of the measuring electrodes to amplify and filter a potential difference between a potential detected by the measuring electrode 211 and a reference potential. FIG. 4 illustrates that a difference between a potential of the measuring electrode 211 and a potential of the reference electrode 214 is amplified when the number of the measuring electrode 211 is one. Configurations of amplifiers and filters for two or more measuring electrodes 211 will be understood by those of ordinary skill in the art. Thus, detailed descriptions are not provided. The circuit of FIG. 4 is just an example, and the inventive concept is not limited thereto.

FIG. 5 illustrates a result of the ABR test conducted by using the hearing aid apparatus 100 of FIG. 1. FIG. 5 illustrates waves of a signal which is detected by the electrode unit 120 and amplified. Signal waveforms in FIG. 5 are normal waveforms of the ABR test. In the graph of FIG. 5, a vertical axis represents a magnitude (μV), and a horizontal axis represents time (msec). Peaks 511 to 516 represent progressive waveforms of respective auditory organs through which a potential generated as a result of the stimulation sound passes from the auditory nerve cells to the brainstem. By comparing waveforms obtained by conducting a test on the user having hearing loss with normal waveforms of FIG. 5, it is determined that hearing ability is not normal when the amplitude of a part of progressive waveforms is excessively small or when a delay time is lengthened. This represents that an auditory organ related to the part of the waveforms is abnormal. Referring to Table 517 in FIG. 5, auditory ranges related to each stage of progressive waveforms are shown. Also, by comparison with normal waveforms, when all waveforms of the ABR are lost, or a delay time of the waveforms I to V is abnormally long, an auditory nerve cell tumor or meningioma may be diagnosed. When a difference between left and right incubation periods for the waveform V is more than about 0.3 msec, retrocochlear lesions may be diagnosed.

Figure 6:
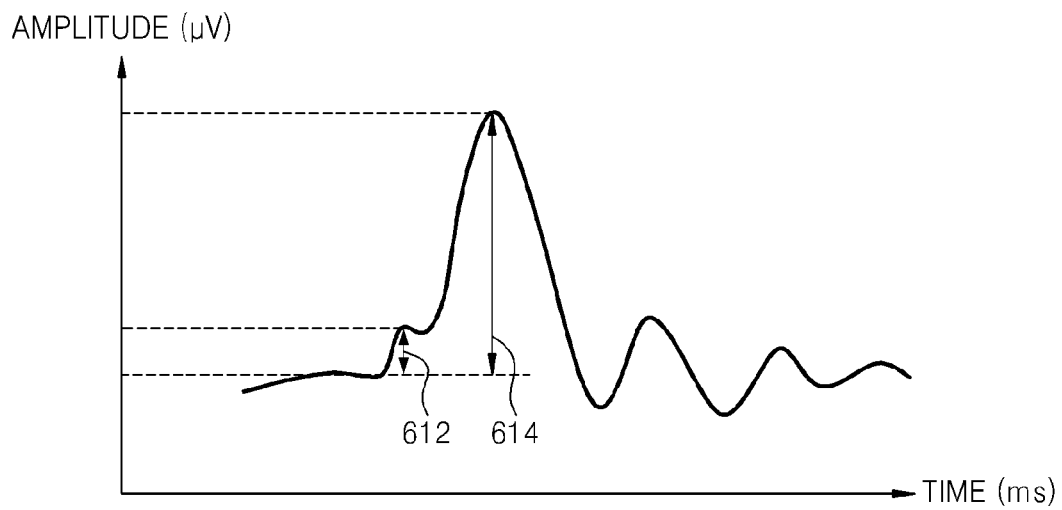
FIG. 6 illustrates waveforms of signals, which are detected by an electrode unit and amplified, as a result of an ECoG test conducted by using the hearing aid apparatus of FIG. 1.

FIG. 6 illustrates waveforms of signals, which are detected by the electrode unit 120 and amplified, as a result of the ECoG test conducted by using the hearing aid apparatus 100 of FIG. 1. Waveforms in FIG. 6 are normal waveforms of the ECoG test. In the graph of FIG. 6, a vertical axis represents a magnitude (μV), and a horizontal axis represents time (msec). The CM, which firstly appears among the three potentials constituting waveforms detected by the electrode 120 according to a result of the ECoG, is rarely used because a variation as a result of electrode position and external noise is large. Thus, the CM may be suppressed using the alternating click phase. Therefore, waves of FIG. 6 include the AP and SP with suppression of the CM. The SP is a DC potential which appears in synchronization with a retention time of a stimulation sound, and has a negative value (−SP). The AP is an AC potential which represents an overall reaction of cochlear nerve fibers. In FIG. 6, 612 represents −SP, and 614 represents AP. As an illustrative example using the result of the ECoG test that uses a ratio of SP to AP (SP/AP ratio), labyrinthine hydrops such as Meniere disease may be diagnosed. Therefore, parameters which represent characteristics of peaks amplified for diagnosing labyrinthine hydrops, such as Meniere disease may be a ratio of magnitudes at the peaks. The processor 160 detects peaks of two waveforms represented by amplified signals as illustrated in FIG. 6. The detected peaks are SP and AP. A peak 612 of a waveform which appears in synchronization with a retention time of a stimulation sound is SP. After the SP appears, a peak 614 that appears within about 5 ms is AP. Next, the processor 160 calculates values for parameters which represent a ratio of values of peaks by using an internal DSP. Values at peaks of SP and AP are obtained, and a ratio therebetween is calculated. That is, the ratio is obtained by dividing 612 by 614. A difference between a value calculated for a ratio of magnitudes of peaks and a target value with which it is determined that labyrinthine hydrops do not exist is obtained to be compared with a permissible range. Thus, labyrinthine hydrops, such as Meniere disease, may be diagnosed. When the value obtained by dividing 612 by 614 is about 0.23 to about 0.27, the value represents normality. On the other hand, when the value is larger than about 0.37, it is determined that labyrinthine hydrops exist. The result of diagnosis of labyrinthine hydrops may be transmitted to an external device using a communication unit 170. Also, the waveforms and the values calculated for parameters of SP/AP ratio waveforms according to the result of ECoG test may be transmitted to an external device through the communication unit 170. However, this is just an example, and the parameters which represent characteristics of peaks amplified by using the ECoG test are not limited to the SP/AP ratio.

Figure 7:
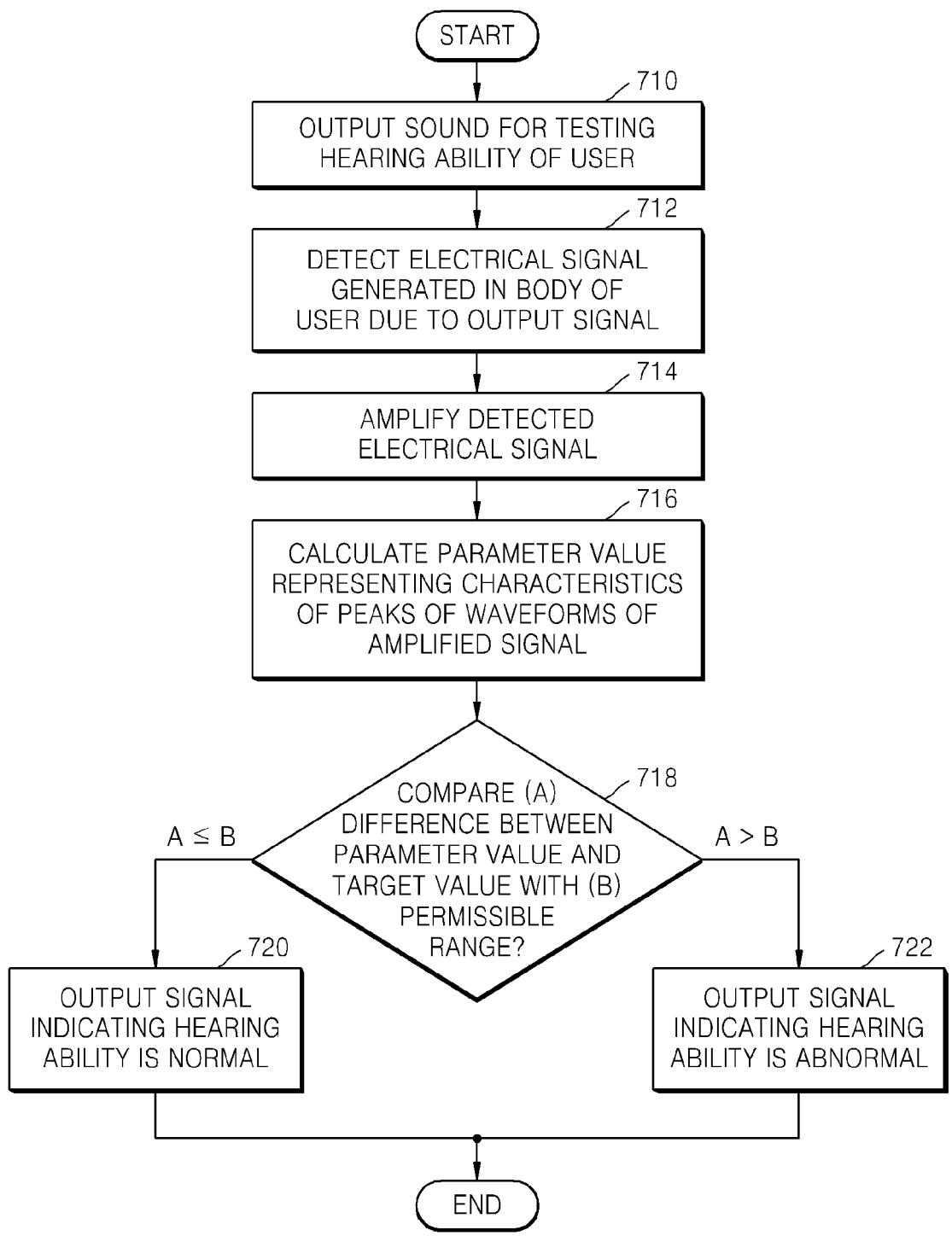
FIG. 7 is a flowchart illustrating an illustrative method of testing hearing ability configured to determine whether hearing ability of a user is normal.

FIG. 7 is a flowchart illustrating a method of determining whether hearing ability of a user is normal using the hearing aid apparatus 100. Referring to FIG. 7, the flowchart includes operations performed by the hearing aid apparatus 100 illustrated in FIG. 1 on a time series basis. Therefore, the above descriptions of the hearing aid apparatus 100 of FIG. 1 may be applied to the method of determining whether hearing ability is normal even though the descriptions are omitted below.

In operation 710, the hearing aid apparatus 100 outputs an auditory stimulation sound for testing the hearing ability of a user. Herein, sounds for the auditory stimulus may include a click, a tone pip, and a tone burst, and the user may select not only the type of the auditory stimulation sound, but also the strength (dB), output interval (times/sec), retention time (pec), and frequency (Hz) of the auditory stimulation sound. The hearing aid apparatus 100 receives the type, strength, output interval, retention time, and frequency of the auditory stimulation sound from the user through the user interface 190, and outputs the type, strength, output interval, retention time, and frequency of the auditory stimulation sound corresponding to the received information.

In operation 712, the hearing aid apparatus 100 detects an electrical signal generated as a result of the auditory stimulation sound output in operation 710. Hereinafter, an electrical signal, which represents the electrical change induced in the body of the user, is referred to as a potential. The hearing aid apparatus 100 acquires a signal required for measuring hearing characteristics of the user using two or more potentials, for example, a potential of the nerve cells and a reference potential thereof. The two or more potentials are detected using two or more electrodes of the electrode unit 120. The electrode unit 120 includes a measuring electrode 211 to detect a potential of the nerve cells, and a reference electrode 214 to detect a potential that is a reference for the potential of the nerve cells. The measuring electrode 211 detects a potential of the nerve cells and the muscle cells. The reference electrode 214 detects a potential which is a reference for a potential detected by the measuring electrode 211. The reference electrode 214 may be used with multiple measuring electrodes 211, and a ground electrode may be used as the reference electrode 214. The reference electrode 214 is located at a position to be least affected by a potential detected by the measuring electrode 211.

In operation 714, the hearing aid apparatus 100 amplifies the potential signals detected in operation 712. Because the detected potential signals are very small signals in units of μV, the hearing aid apparatus 100 amplifies the detected signals to measure the user's hearing characteristics using the potential signals. The hearing aid apparatus 100 receives the reference potential detected by the reference electrode 214 and the potential detected by the measuring electrode 211 to amplify a difference therebetween. The hearing aid apparatus 100 may perform a filtering operation for cutting off a frequency by amplifying a difference between potentials to acquire an amplified signal of a desired frequency band.

In operation 716, the hearing aid apparatus 100 calculates parameters which represent characteristics of peaks of waveforms of the signal amplified in operation 714. For example, the calculated values may be the hearing characteristics of the user. Also, the parameters that represent the characteristics of peaks may be generation times of the peaks, signal magnitudes at the peaks, and ratio of peaks. Hereinafter, for illustrative purposes, it is assumed that the parameters that represent characteristics of peaks are signal magnitudes at the peaks. To calculate values of signal magnitudes at peaks of waveforms of the signal amplified in operation 714, the hearing aid apparatus 100 detects the peaks of waveforms of the signal amplified in operation 714. For instance, the hearing aid apparatus 100 may detect the peaks by obtaining one arbitrary point (n) for a certain time and by comparing a magnitude of the arbitrary point (n) with that of another point (n-dt). However, the detection of peaks is not limited thereto, and it will be understood by those of ordinary skill in the art that various alternative algorithms may be used. Next, at operation 716, parameter values for signal magnitudes at peaks are calculated. The hearing aid apparatus 100 outputs a sound to test the hearing ability of the user for each of a plurality of frequencies, detects peaks of signals amplified and input for each of a plurality of frequencies, and calculates values of signal magnitudes to obtain the values calculated for each of the plurality of frequencies.

In operation 718, the hearing aid apparatus 100 determines whether hearing ability is normal by comparing a difference between the parameter value calculated in operation 716 and a target value and determining whether the difference is within a permissible range. Herein, the target value is acquired by measuring hearing characteristics of people having normal hearing ability by using the hearing aid apparatus 100. The hearing aid apparatus 100 calculates values of signal magnitudes at the peaks of waveforms of amplified signals by detecting potential signals generated in bodies of people having normal hearing ability. The calculated values represent hearing characteristic of people having normal hearing ability, and an average of the calculated values is the target value. If the hearing characteristics of the user are included in the permissible range, the hearing ability of the user is normal. If the hearing characteristics of the user are not included in the permissible range, the hearing ability of the user is abnormal. Thus, the predetermined permissible range is a reference for determining whether the hearing ability of the user is normal. That is, the predetermined permissible range is a normal range of hearing ability. The normal range of hearing ability may be determined using various methods.

For instance, the normal range of hearing ability may be determined by calculating standard error using standard deviation and sample size of calculated values, which represent hearing characteristics of people having normal hearing ability. The sample size represents the number of people having normal hearing ability. The method of calculating standard error using standard deviation and sample size will be understood by those of ordinary skill in the art, and, thus, detailed descriptions thereof are omitted. It will be understood by those of ordinary skill in the art that the normal range of hearing ability is not limited to the above described calculation method by using the standard error, and there are various other methods. Also, the hearing aid apparatus 100 compares the values calculated in operation 716 for each of the plurality of frequencies with a target value for each frequency to determine whether the hearing ability of the user is normal for each frequency.

In operation 720, the hearing aid apparatus 100 determines that the hearing ability of the user is normal if a difference between the calculated value and the target value is within a permissible range on the basis of a result of the comparison in operation 718. The hearing aid apparatus 100 outputs a signal which indicates that hearing ability is normal when it is determined that the hearing ability is normal. The hearing aid apparatus 100 may inform the user that the hearing ability is normal with a sound according to the signal that indicates that the hearing ability is normal. The hearing aid apparatus 100 may output the signal, which indicates that the hearing ability is normal, to an external device (not illustrated) to inform the user that the hearing ability is normal through the external device.

In operation 722, the hearing aid apparatus 100 determines that the hearing ability of the user is abnormal if a difference between the calculated value and the target value is out of a permissible range on the basis of a result of the comparison in operation 718. Abnormal hearing ability means that there is loss in the hearing ability of the user. Abnormality of hearing ability may be indicative that a particular auditory organ is abnormal or there may be a particular auditory disease according to specifically measured hearing characteristics of the user, for instance, according to a kind of parameter which represents characteristics of peaks. The hearing aid apparatus 100 outputs a signal which indicates that the hearing ability is abnormal when it is determined that the hearing ability is abnormal. For instance, the hearing aid apparatus 100 may inform the user that the hearing ability is abnormal with a sound according to the signal which indicates that the hearing ability is abnormal. The hearing aid apparatus 100 may output the signal, which indicates that the hearing ability is abnormal, to an external device (not illustrated) to inform the user that the hearing ability is abnormal. Also, the hearing aid apparatus 100 may transmit the waveforms of the signal amplified in operation 716 and the values calculated in operation 718, for example, hearing characteristics of the user, and data of the result of comparing the values calculated in operation 720 and a target value of hearing ability to an external device (not illustrated) with the signal indicating that the hearing ability is abnormal. The hearing aid apparatus 100 determines whether the hearing ability is normal by outputting corresponding signals according to whether the hearing ability is normal, and completes the above described operations.

Figure 8:
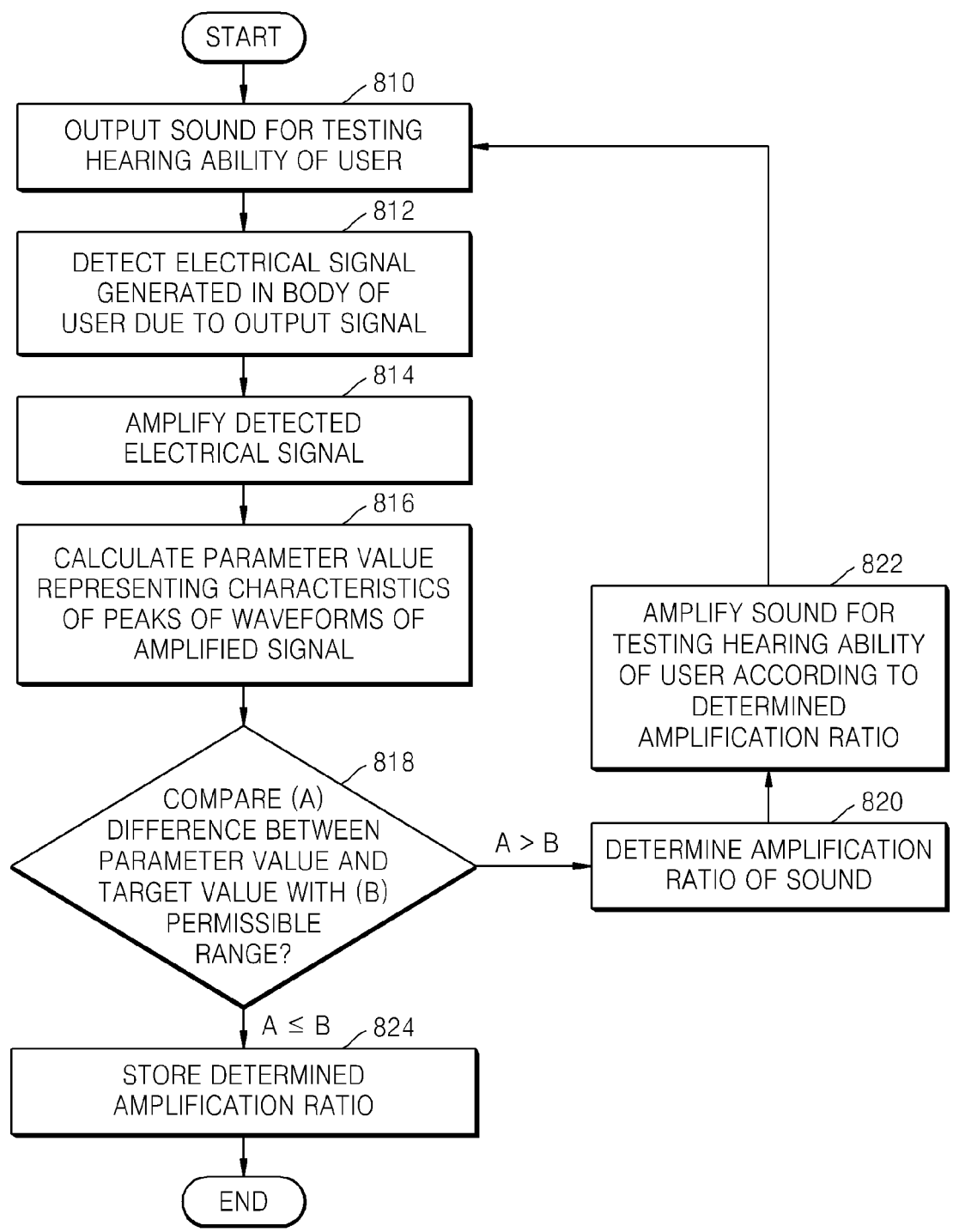
FIG. 8 is a flowchart illustrating an illustrative configuration of a method to determine an amplification ratio to compensate for hearing loss of a user using the hearing aid apparatus of FIG. 1.

FIG. 8 is a flowchart illustrating a method of optimally compensating for hearing loss of a user using the hearing aid apparatus 100. Referring to FIG. 8, the flowchart includes operations performed using the hearing aid apparatus 100 illustrated in FIG. 1 to determine an amplification ratio that optimally compensates for the user's hearing loss on a time series basis. Therefore, the above descriptions of the hearing aid apparatus 100 of FIG. 1 may be applied to the method of determining an amplification ratio that optimally compensates for the hearing loss of the user even though some descriptions may be omitted below.

In operation 810, the hearing aid apparatus 100 outputs a signal of an auditory stimulation sound for testing the hearing ability of the user. The hearing aid apparatus 100 receives the type, strength, output interval, retention time, and frequency of the auditory stimulation sound from the user through the user interface 190 operatively connected to the hearing aid apparatus 100, and outputs the type, strength, output interval, retention time, and frequency of the auditory stimulation sound corresponding to the received information.

In operation 812, the hearing aid apparatus 100 detects an electrical signal generated as a result of the auditory stimulation sound output in operation 810. The hearing aid apparatus 100 acquires the electrical signal to be used to measure the hearing characteristics of the user using two or more potentials, for example, a potential of the nerve cells and a reference potential thereof.

In operation 814, the hearing aid apparatus 100 amplifies the potential signals detected in operation 812. Because the detected potential signals are very small signals in units of µV, the hearing aid apparatus 100 amplifies the detected signals to measure the hearing characteristics of the user using the potential signals. The hearing aid apparatus 100 receives the reference potential detected by the reference electrode 214 and the potential detected by the measuring electrode 211 to amplify a difference therebetween. The hearing aid apparatus 100 may perform a filtering operation to cut off a frequency by amplifying a difference between the potentials signals and acquire an amplified signal of a desired frequency band.

In operation 816, the hearing aid apparatus 100 calculates parameters that represent characteristics of peaks of waveforms of the signal amplified in operation 814. The calculated values may be hearing characteristics of the user. In an example, the parameters that represent the characteristics of peaks may be generation times of the peaks, signal magnitudes at the peaks, and ratio of peaks. Hereinafter, for illustrative purposes, it is assumed that the parameters that represent characteristics of peaks are signal magnitudes at the peaks. To calculate values of signal magnitudes at peaks of waveforms of the signal amplified in operation 814, the hearing aid apparatus 100 detects the peaks of waveforms of the signal amplified in operation 816. Next, values for signal magnitudes at peaks are calculated. The hearing aid apparatus 100 outputs a sound to test the hearing ability of the user for each of a plurality of frequencies, detects peaks of signals amplified and input for each of a plurality of frequencies, and calculates values of signal magnitudes to obtain the values calculated for each of the plurality of frequencies.

In operation 818, the hearing aid apparatus 100 compares a difference between the parameter value calculated in operation 816 and a target value with a permissible range. For instance, the target value may be acquired by measuring hearing characteristics of people having normal hearing ability by using the hearing aid apparatus 100. The hearing aid apparatus 100 calculates values of signal magnitudes at the peaks of waveforms of amplified signals by detecting potential signals generated in bodies of people having normal hearing ability. The calculated values represent hearing characteristic of people having normal hearing ability, and an average of the calculated values is the target value. Therefore, the hearing ability of the user is closer to normality as the calculated values, for example, the hearing characteristics of the user, may be closer to a target value. For determining or producing an amplification ratio that optimally compensates for hearing loss, the amplification ratio may be close to a target value. The predetermined permissible range may be a reference to determine whether the hearing ability of the user is normal. However, for illustrative purposes, in this method, the predetermined permissible range may be a reference for determining an amplification ratio that optimally compensates for hearing ability. The peak levels of the electrical signal generated as a result of the output sound (eg. ABR) may depend on the level of test input audio signal. The louder test input audio signal should induce the larger (or more) peak levels of the measured electrical signal. For the hearing impaired, test input audio signal to obtain normal-like morphology of the electrical signal from the electrodes should be louder. In one example, permissible range is a morphology of output electrical signal of the hearing impaired (for example, the ratio of each peak level such as peak I/peak II, peak III/peak II in ABR) is similar with or approximate to the one of normal person.

Therefore, to determine or produce an amplification ratio that optimally compensates for hearing loss, the predetermined permissible range may be reduced so that the amplification ratio is close to the target value. In circumstances when the amplification ratio of the hearing aid apparatus 100 is close to the target value, the hearing aid apparatus 100 is most appropriately compensating for hearing loss. Also, the hearing aid apparatus 100 may compare the values calculated in operation 816 for each of a plurality of frequencies with a target value for each frequency to calculate a difference therebetween. According to a result of the comparison, when the difference between the values calculated in operation 816 and a target value is within the predetermined permissible range, operation 824 is performed. Otherwise, operation 820 is performed.

In operation 820, the hearing aid apparatus 100 determines an amplification ratio for the auditory stimulation sound detected by the hearing aid apparatus 100 when the difference between the calculated value and the target value is out of the predetermined permissible range based on a result of the comparison in operation 818. The hearing aid apparatus 100 calculates and determines the amplification ratio according to the difference between the parameter value calculated in operation 816 and the target value. The sound amplification ratio may be calculated using hearing characteristics of people having hearing loss. For instance, by measuring calculated values that represent hearing characteristics of people having hearing loss using the hearing aid apparatus 100, and by comparing the measured values with a sound amplification ratio that is determined using a typical test method and is for people having hearing loss, a formula may be obtained to convert a difference between the calculated value for people having hearing loss and a target value to a sound amplification ratio. With this formula, a sound amplification ratio may be determined. Also, the hearing aid apparatus 100 may determine an amplification ratio for each of a plurality of frequencies by calculating a sound amplification ratio for each frequency on the basis of the values calculated in operation 816.

In operation 822, the hearing aid apparatus 100 amplifies an auditory stimulation sound output for testing hearing ability according to an amplification ratio determined in operation 820. The hearing aid apparatus 100 goes back to operation 810 to output an auditory stimulation sound amplified in operation 822. The hearing aid apparatus 100 may determine a sound amplification ratio with which the hearing loss of the user is optimally compensated for by repeating the above-described processes according to an auditory stimulation sound amplified in operation 822. The amplification ratio, which optimally compensates for the hearing loss, may be obtained by repeating the above-described processes to test whether an amplification ratio appropriately compensates for the hearing loss. The above-described processes may be repeated a predetermined number of times to find an amplification ratio with which the hearing loss of the user is most appropriately compensated for. At the same time, the value calculated in operation 816 may be included in the predetermined permissible range, and closest to a target value.

In operation 824, the hearing aid apparatus 100 stores the amplification ratio newly determined in operation 820 when the difference between the calculated value and the target value is within the predetermined permissible range based on a result of the comparison in operation 818. The hearing aid apparatus 100 stores an amplification ratio newly determined in operation 820, and compensates for the user's hearing loss according to the newly determined amplification ratio. That is, the hearing aid apparatus 100 amplifies and outputs a surrounding sound detected by the hearing aid apparatus 100 according to the newly determined amplification ratio so that the user may hear the amplified sound. Also, the hearing aid apparatus 100 may update an amplification ratio for each frequency. The hearing aid apparatus 100 stores the amplification ratio determined in operation 820 and completes the above-described processes.

Meanwhile, the method of testing hearing ability and the method of compensating for hearing loss may be programmed to be executed by a computer. A computing system or the computer may include a microprocessor that is electrically connected with a bus, a user interface, and a memory controller. It may further include a flash memory device. The flash memory device may store N-bit data via the memory controller. The N-bit data is processed or will be processed by the microprocessor and N may be 1 or an integer greater than 1. Where the computing system or computer is a mobile apparatus, a battery may be additionally provided to supply operation voltage of the computing system or computer. It will be apparent to those of ordinary skill in the art that the computing system or computer may further include an application chipset, a camera image processor (CIS), a mobile Dynamic Random Access Memory (DRAM), and the like. The memory controller and the flash memory device may constitute a solid state drive/disk (SSD) that uses a non-volatile memory to store data.

Furthermore, the method of testing hearing ability and the method of compensating for hearing loss may be implemented in a general digital computer which executes the program using a non-transitory computer readable medium. Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable storage mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. Also, the described units in FIGS. 1 and 9 to perform an operation or a method may be hardware, software, or some combination of hardware and software. For example, the unit may be a software package running on a computer or the computer on which that software is running.

Figure 9:
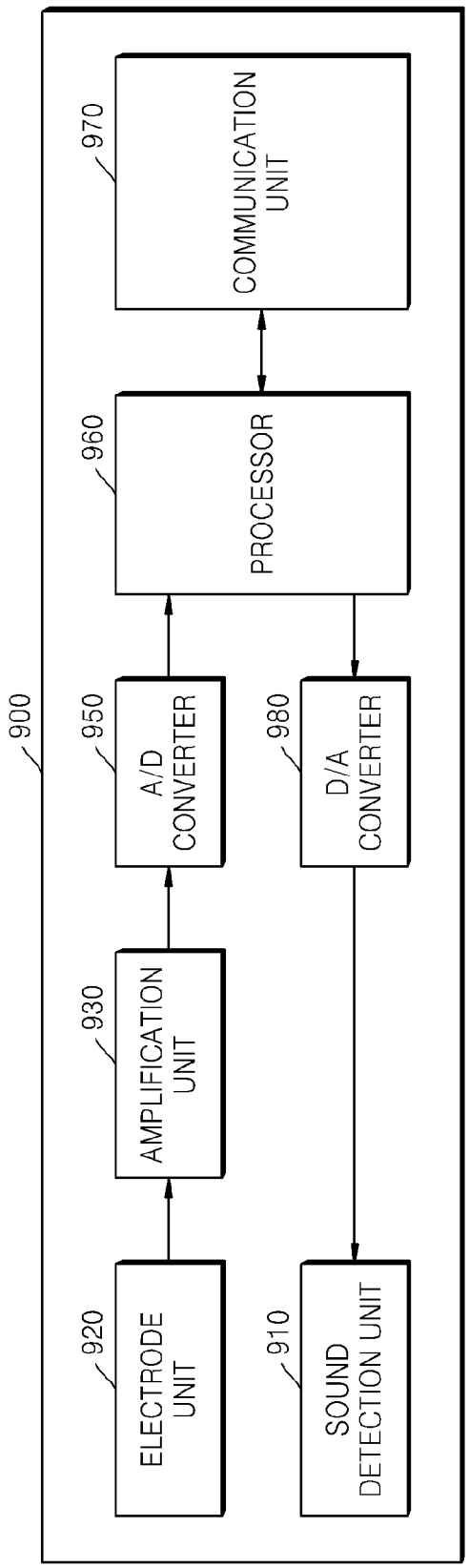
FIG. 9 is a block diagram illustrating a hearing test device using the method of testing hearing ability of FIG. 7.

FIG. 9 is a block diagram illustrating a hearing test device 900 according to the hearing aid apparatus 100 illustrated in FIG. 1. The hearing test device 900 illustrated in FIG. 9 performs an objective hearing test to determine whether a user's hearing ability is normal. The hearing test device 900 illustrated in FIG. 9 includes the components of the hearing aid apparatus 100 illustrated in FIG. 1 except for the sound detection unit 140. That is, the hearing test device 900 may include a sound output unit 910, an electrode unit 920, an amplification unit 930, an analog-to-digital (A/D) converter 950, a processor 960, a communication unit 970, and a digital-to-analog (D/A) converter 980. Since the sound output unit 910, electrode unit 920, amplification unit 930, A/D converter 950, communication unit 970, and D/A converter 980 of the hearing test device 900 respectively perform the same operations as the sound output unit 110, electrode unit 120, amplification unit 130, A/D converter 150, communication unit 170, and D/A converter 180 of the hearing aid apparatus 100, detailed descriptions thereof are omitted. The processor 960 performs the operations of the processor 160 except for the operation of outputting a hearing-loss-compensated sound by determining an amplification ratio to compensate for the hearing loss and by detecting surrounding sound. Therefore, the operations performed at the processor 960 to measure hearing characteristics of the user and to determine whether the hearing ability is normal are the same as those of the processor 160, and, thus, detailed descriptions thereof are omitted. Also, the operations of measuring the hearing characteristics of the user and determining whether the hearing ability of the user is normal of the hearing test device 900 are the same as those of the hearing aid apparatus 100, and thus detailed descriptions thereof are omitted.

According to embodiments of the inventive concept, waveforms of electrical signals generated in a body of a user are acquired using an electrode of a hearing aid apparatus, and determined processor determines whether the hearing ability of the user is normal based on characteristics of peaks of the waveforms of the signals. Thus, a hearing test is easily and rapidly conducted, and an objective and quantitative result of the hearing test is obtained. Also, an amplification ratio for the sound detected by the hearing aid apparatus is determined on the basis of characteristics of peaks of waveforms of signals acquired by using the electrode of the hearing aid apparatus. Therefore, correct and rapid compensation for hearing loss is possible by virtue of the quantitative and objective result of the hearing test described above. Also, the hearing test may check whether the determined amplification ratio appropriately compensates for the hearing loss of the user.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A hearing aid apparatus, comprising:
a sound output unit configured to output a sound to test a hearing ability of a user;
an electrode unit configured to detect an electrical signal generated in a body of the user as a result of the output sound;
an amplification unit configured to amplify the electrical signal detected by the electrode unit; and
a processor configured to calculate a value of a parameter, which represents characteristics of peaks of waveforms of the amplified signal, and to determine an amplification ratio of a surrounding sound detected by the hearing aid apparatus based on a difference between the value of the parameter and a target value,
wherein the sound output unit outputs the sound to test the hearing ability of the user after the sound is amplified based on the amplification ratio determined by the processor, and the processor repeats the determining of the amplification ratio until the difference between the value of the parameter and the target value is lower than a predetermined permissible range using the electrical signal generated as a result of the output sound.

2. The hearing aid apparatus of claim 1, wherein the characteristics of the peaks comprise one or more generation times of the peaks and signal magnitudes at the peaks.

3. The hearing aid apparatus of claim 1, wherein the target value comprises an average of parameter values calculated for people having normal hearing ability.

4. The hearing aid apparatus of claim 1, wherein the processor determines an optimal amplification ratio to be the amplification ratio, among amplification ratios determined during the repetition, with a parameter value closest to the target value.

5. The hearing aid apparatus of claim 1, wherein the processor determines that the hearing ability of the user is abnormal when the difference between the value of the parameter and the target value is out of a predetermined permissible range, and outputs a signal indicating that the hearing ability of the user is abnormal.

6. The hearing aid apparatus of claim 5, wherein the sound output unit is configured to receive the signal indicating that the hearing ability of the user is abnormal, and to output a sound indicating that the hearing ability of the user is abnormal.

7. The hearing aid apparatus of claim 1, wherein the sound output unit outputs the sound for each of a plurality of frequencies, and the processor determines the amplification ratio of the detected surrounding sound for each of the plurality of frequencies based on the characteristics of the peaks of the waveforms of the amplified signal for each of the plurality of frequencies.

8. A method of testing hearing ability, the method comprising:
receiving an electrical signal generated in a body of a user as a result of a sound to test the hearing ability of the user;
calculating a value of a parameter representing characteristics of peaks of waveforms of the electrical signal;
comparing the value of the parameter with a target value; and
determining that the hearing ability is abnormal when a difference between the value of the parameter and the target value is out of a predetermined permissible range.

9. The method of testing hearing ability of claim 8, further comprising:
configuring the characteristics of the peaks to comprise one or more generation times of the peaks and signal magnitudes at the peaks.

10. The method of testing hearing ability of claim 8, further comprising:
configuring the target value to be an average of parameter values calculated for people having normal hearing ability.

11. The method of testing hearing ability of claim 8, further comprising:
repeating the receiving of the electrical signal, the calculating of the value of the parameter, the comparing of the value of the parameter with the target value, and the determining of whether the hearing ability is normal for each of a plurality of frequencies, and
determining whether the hearing ability of the user is normal for each of the plurality of frequencies.

12. The method of testing hearing ability of claim 11, further comprising:
integrating values of parameters repeatedly calculated for each of the plurality of frequencies to provide information related to the hearing ability of the user.

13. The method of testing hearing ability of claim 8, further comprising:
    outputting a signal configured to indicate that the hearing ability of the user is abnormal when it is determined that the hearing ability of the user is abnormal.

14. The method of testing hearing ability of claim 8, further comprising:
    detecting the electrical signal using an electrode disposed on a tympanum or an external auditory meatus of the user.

15. The method of testing hearing ability of claim 8, further comprising:
    detecting the electrical signal using an electrode disposed on a forehead or a scalp of the user.

16. A non-transitory computer readable medium having stored therein a computer program configured to control a processor to execute: receiving an electrical signal generated in a body of a user as a result of a sound to test a hearing ability of the user;
    calculating a value of a parameter representing characteristics of peaks of waveforms of the electrical signal;
    comparing the value of the parameter with a target value; and
    determining that the hearing ability is abnormal when a difference between the value of the parameter and the target value is out of a predetermined permissible range.

17. A method to compensate for hearing loss of a user using a hearing aid, comprising:
    outputting a signal of an auditory stimulation sound to test a hearing ability of the user;
    detecting an electrical signal as a result of the auditory stimulation sound;
    amplifying the electrical signal detected;
    calculating a parameter value representing characteristics of peaks of waveforms of the electrical signal amplified;
    comparing a difference between the parameter value and a target value with a predetermined range;
    determining an amplification ratio for the auditory stimulation sound based on the difference between the parameter value and the target value; and
    amplifying an auditory stimulation sound output for testing the hearing ability of the user based on the amplification ratio determined
    repeating the outputting the signal, the detecting the electrical signal, the amplifying the electrical signal detected, the calculating the parameter value, the comparing the difference between the parameter value and the target value, the determining an amplification ratio, and the amplifying the auditory stimulation sound output until the difference between the value of the parameter and the target value is lower than a predetermined permissible range.

* * * * *